US012670731B2

(12) United States Patent (10) Patent No.: US 12,670,731 B2
Tanaka (45) Date of Patent: Jun. 30, 2026

(54) ALCOHOL DETECTION APPARATUS

(71) Applicant: SUBARU CORPORATION, Tokyo (JP)

(72) Inventor: Atsuya Tanaka, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 322 days.

(21) Appl. No.: 18/404,597

(22) Filed: Jan. 4, 2024

(65) Prior Publication Data
US 2024/0242515 A1 Jul. 18, 2024

(30) Foreign Application Priority Data
Jan. 18, 2023 (JP) ................................. 2023-005930

(51) Int. Cl.
*G06V 20/59* (2022.01)
*A61B 5/00* (2006.01)
(Continued)

(52) U.S. Cl.
CPC .......... *G06V 20/597* (2022.01); *A61B 5/0077* (2013.01); *A61B 5/082* (2013.01);
(Continued)

(58) Field of Classification Search
CPC ................ G06V 20/597; G06V 40/107; A61B 2503/22; A61B 5/4824; A61B 5/7282;
(Continued)

(56) References Cited

U.S. PATENT DOCUMENTS

2005/0074142 A1* 4/2005 Ertl ................... B60R 21/01538
                                                              382/104
2008/0316037 A1 12/2008 Shoji et al.
                        (Continued)

FOREIGN PATENT DOCUMENTS

CN        112216030 A * 1/2021 ............. G06V 40/20
CN        112895895 A * 6/2021 ........... G01N 21/359
                        (Continued)

OTHER PUBLICATIONS

European Search Report issued in European Patent Application No. 24 15 1088 dated Jun. 4, 2024.

*Primary Examiner* — John Villecco
*Assistant Examiner* — Kyla Guan-Ping Tiao Allen
(74) *Attorney, Agent, or Firm* — TROUTMAN PEPPER LOCKE LLP

(57) ABSTRACT
An alcohol detection apparatus includes an image sensor, a touch sensor, an alcohol sensor, and a processor. The image sensor generates a captured image by performing imaging of an occupant in a driver's seat of a vehicle. The alcohol sensor performs a detection of an alcohol component in breath of the occupant. Based on the captured image, the processor performs a first process of confirming whether the occupant is touching the touch sensor, and performs a second process of confirming whether the occupant is holding the alcohol sensor. The processor performs a determination process of determining that a result of the detection obtainable by the alcohol sensor is effective when conditions are satisfied. The conditions include that the occupant is touching the touch sensor in the first process and that the occupant is holding the alcohol sensor in the second process.

7 Claims, 3 Drawing Sheets

(51) Int. Cl.

| | |
|---|---|
| *A61B 5/08* | (2006.01) |
| *A61B 5/18* | (2006.01) |
| *G01N 33/497* | (2006.01) |
| *G06T 7/70* | (2017.01) |
| *G06V 40/10* | (2022.01) |

(52) U.S. Cl.
CPC .............. *A61B 5/18* (2013.01); *A61B 5/4845* (2013.01); *A61B 5/6893* (2013.01); *G06T 7/70* (2017.01); *G06V 40/107* (2022.01); *G01N 33/4972* (2013.01); *G06T 2207/30201* (2013.01); *G06T 2207/30268* (2013.01)

(58) Field of Classification Search
CPC ......... A61B 5/0077; A61B 5/082; A61B 5/18; A61B 5/4845; A61B 5/6893; H04N 23/50; H04N 25/70; B60K 28/063; G06T 7/70; G06T 2207/30201; G06T 2207/30268; G01N 33/4972
See application file for complete search history.

(56) References Cited

U.S. PATENT DOCUMENTS

| | | | |
|---|---|---|---|
| 2015/0165903 A1 | 6/2015 | Williams et al. | |
| 2018/0326992 A1* | 11/2018 | Aoi ...................... | G06V 20/597 |
| 2020/0122731 A1* | 4/2020 | Vanhelle ............... | B60W 50/12 |
| 2022/0028009 A1* | 1/2022 | Chan ..................... | G06Q 40/08 |
| 2022/0169152 A1 | 6/2022 | Kim | |
| 2023/0067020 A1* | 3/2023 | Ono .................... | A61B 5/4845 |

FOREIGN PATENT DOCUMENTS

| | | | | |
|---|---|---|---|---|
| JP | 2005-297816 A | 10/2005 | | |
| JP | 2009-113708 A | 5/2009 | | |
| JP | 2009136393 A | * 6/2009 | ............. | F25B 13/00 |
| JP | 2009-274563 A | 11/2009 | | |
| JP | 2014-2162 A | 1/2014 | | |

* cited by examiner

ALCOHOL DETECTION APPARATUS

CROSS-REFERENCE TO RELATED APPLICATION

The present application claims priority from Japanese Patent Application No. 2023-005930 filed on Jan. 18, 2023, the entire contents of which are hereby incorporated by reference.

BACKGROUND

The disclosure relates to an alcohol detection apparatus configured to detect an alcohol component included in breath of an occupant.

Many vehicles are provided with an apparatus configured to detect whether an occupant has dunk alcohol. For example, Japanese Unexamined Patent Application Publication No. 2014-002162 discloses an apparatus configured to detect an alcohol component included in breath of an occupant.

SUMMARY

An aspect of the disclosure provides an alcohol detection apparatus that includes an image sensor, a touch sensor, an alcohol sensor, and a processor. The image sensor is configured to generate a captured image by performing imaging of a first occupant in a driver's seat of a vehicle. The touch sensor is provided at the driver's seat and is configured to perform a detection of a touch. The alcohol sensor is configured to perform a detection of an alcohol component included in breath of the first occupant. The processor is configured to perform processes based on the captured image generated by the image sensor, a result of the detection performed by the touch sensor, and a result of the detection performed by the alcohol sensor. The processor is configured to perform a first process of confirming, based on the captured image, whether the first occupant in the driver's seat is touching the touch sensor. The processor is configured to perform a second process of confirming, based on the captured image, whether the first occupant in the driver's seat is holding the alcohol sensor. The processor is configured to perform a determination process of determining that the result of the detection obtainable by the alcohol sensor is effective when a plurality of conditions is satisfied. The plurality of conditions includes that the first occupant is touching the touch sensor in the first process and that the first occupant is holding the alcohol sensor in the second process.

BRIEF DESCRIPTION OF THE DRAWINGS

The accompanying drawings are included to provide a further understanding of the disclosure, and are incorporated in and constitute a part of this specification. The drawings illustrate embodiments and, together with the specification, serve to explain the principles of the disclosure.

DETAILED DESCRIPTION

Figure 1:
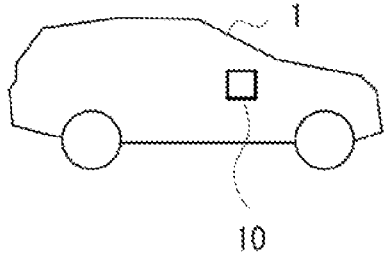
FIG. 1 is an explanatory diagram illustrating a configuration example of a vehicle according to one example embodiment of the disclosure.

Regarding a vehicle, it may be desired to detect whether an occupant of the vehicle has drunk alcohol, and it may be expected to more effectively detect whether the occupant has drunk alcohol.

It is desirable to provide an alcohol detection apparatus configured to more effectively detect whether an occupant has drunk alcohol.

In the following, some example embodiments of the disclosure are described in detail with reference to the accompanying drawings. Note that the following description is directed to illustrative examples of the disclosure and not to be construed as limiting to the disclosure. Factors including, without limitation, numerical values, shapes, materials, components, positions of the components, and how the components are coupled to each other are illustrative only and not to be construed as limiting to the disclosure. Further, elements in the following example embodiments which are not recited in a most-generic independent claim of the disclosure are optional and may be provided on an as-needed basis. The drawings are schematic and are not intended to be drawn to scale. Throughout the present specification and the drawings, elements having substantially the same function and configuration are denoted with the same reference numerals to avoid any redundant description. In addition, elements that are not directly related to any embodiment of the disclosure are unillustrated in the drawings.

Figure 2:
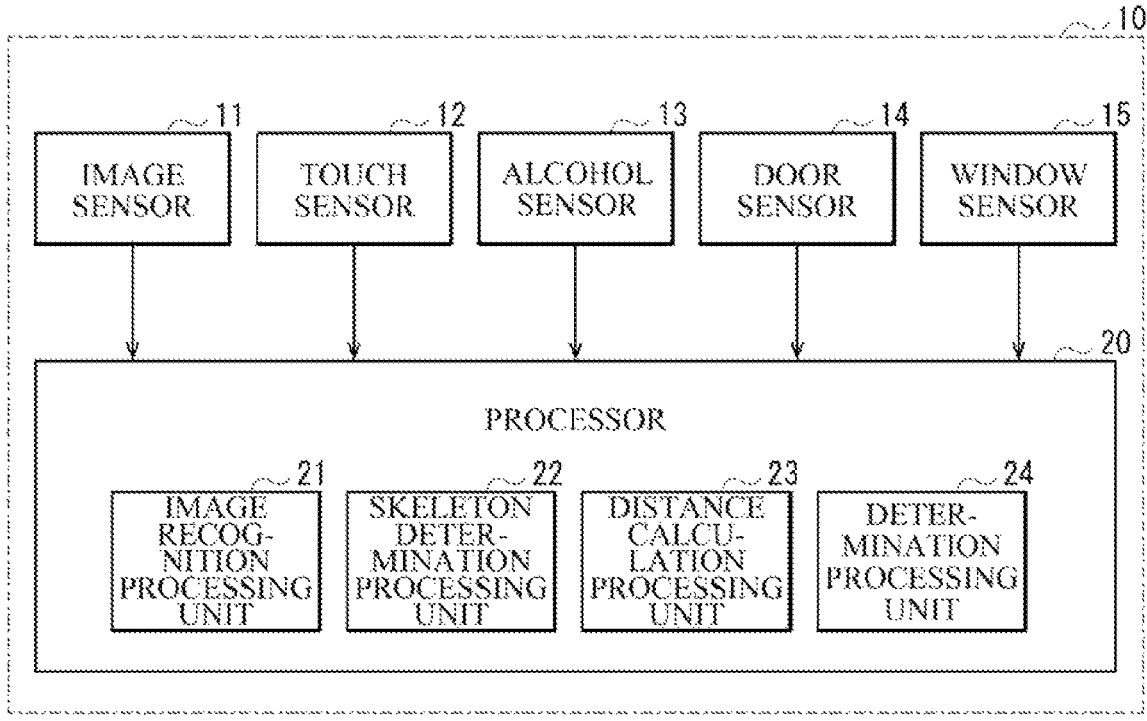
FIG. 2 is a block diagram illustrating a configuration example of an alcohol detection apparatus illustrated in FIG. 1.

FIG. 1 illustrates a configuration example of a vehicle 1 provided with an alcohol detection apparatus according to an example embodiment of the disclosure. The vehicle 1 may include an alcohol detection apparatus 10. FIG. 2 illustrates a configuration example of the alcohol detection apparatus 10.

The alcohol detection apparatus 10 may include an image sensor 11, a touch sensor 12, an alcohol sensor 13, a door sensor 14, a window sensor 15, and a processor 20.

The image sensor 11 may be configured to generate a captured image by performing imaging of an inside of the vehicle 1. For example, the image sensor 11 may be configured to perform imaging of an occupant seated in a seat such as a driver's seat or a passenger seat.

The touch sensor 12 may be provided at a steering wheel of the vehicle 1. The touch sensor 12 may be configured to perform a detection of a touch of a driver who is an occupant seated in the driver's seat. In this example, the driver holding the steering wheel may cause, for example, a finger tip of the driver to touch a detection surface of the touch sensor 12.

The alcohol sensor 13 may be configured to perform a detection of an alcohol component included in breath of the driver. For example, the driver breathing into a blowing port of the alcohol sensor 13 may allow the alcohol sensor 13 to detect an alcohol component included in the breath of the driver. The alcohol sensor 13 may include a housing having a surface provided with a marker. For example, the marker may include a reflective material. Note that the configuration of the marker is not limited thereto, and in one example, the marker may include a graphical pattern. The alcohol detection apparatus 10 may be configured to recognize the alcohol sensor 13 based on an image of the marker included in the captured image generated by the image sensor 11, as will be described later.

The door sensor 14 may be configured to perform a detection of an open state and a closed state of a door of the vehicle 1. The window sensor 15 may be configured to perform a detection of an open state and a closed state of a window of the vehicle 1.

The processor 20 may be configured to perform a process of permitting or forbidding the driver to drive the vehicle 1, based on an amount of the alcohol component included in the breath of the driver. For example, the processor 20 may include one or more processors and one or more memories, and may be configured to execute a program to perform processes. The processor 20 may include an image recognition processing unit 21, a skeleton determination processing unit 22, a distance calculation processing unit 23, and a determination processing unit 24.

The image recognition processing unit 21 may be configured to perform an image recognition process based on the captured image supplied from the image sensor 11. For example, the image recognition processing unit 21 may perform the image recognition process to detect the driver seated in the driver's seat and detect the alcohol sensor 13 based on the marker of the alcohol sensor 13.

The skeleton determination processing unit 22 may be configured to perform a skeleton determination process regarding the driver based on the captured image supplied from the image sensor 11. For example, the skeleton determination processing unit 22 may perform the skeleton determination process to detect that the driver is holding the steering wheel by one hand and that the driver is holding the alcohol sensor 13 by another hand.

The distance calculation processing unit 23 may be configured to perform a distance calculation process based on the captured image supplied from the image sensor 11. For example, the distance calculation processing unit 23 may be configured to, when the driver is breathing into the blowing port of the alcohol sensor 13, calculate a distance from the driver's face to the blowing port of the alcohol sensor 13 based on the captured image.

The determination processing unit 24 may be configured to determine whether a result of the detection obtainable by the alcohol sensor 13 is effective, based on respective results of the processes performed by the image recognition processing unit 21, the skeleton determination processing unit 22, and the distance calculation processing unit 23. When the determination processing unit 24 determines that the result of the detection obtainable by the alcohol sensor 13 is effective and the amount of the alcohol component detected by the alcohol sensor 13 is less than or equal to a predetermined amount, the determination processing unit 24 may perform a process of permitting the driver to drive the vehicle 1. In this case, for example, the determination processing unit 24 may allow an engine of the vehicle 1 to be started. When the determination processing unit 24 determines that the result of the detection obtainable by the alcohol sensor 13 is effective and the amount of the alcohol component detected by the alcohol sensor 13 is not less than or equal to the predetermined amount, or when the determination processing unit 24 determines that the result of the detection obtainable by the alcohol sensor 13 is not effective, the determination processing unit 24 may perform a process of forbidding the driver to drive the vehicle 1. In this case, for example, the determination processing unit 24 may inhibit the engine of the vehicle 1 from being started.

In one embodiment, the image sensor 11 may serve as an "image sensor". In one embodiment, the touch sensor 12 may serve as a "touch sensor". In one embodiment, the alcohol sensor 13 may serve as an "alcohol sensor". In one embodiment, the processor 20 may serve as a "processor".

Next, an operation and workings of the alcohol detection apparatus 10 according to the example embodiment will be described.

First, the operation of the alcohol detection apparatus 10 will be described with reference to FIG. 2. The image sensor 11 may generate a captured image by performing imaging of the inside of the vehicle 1. The touch sensor 12 may perform a detection of a touch of the driver who is the occupant seated in the driver's seat. The alcohol sensor 13 may perform a detection of the alcohol component included in the breath of the driver. The door sensor 14 may perform a detection of the open state and the closed state of the door of the vehicle 1. The window sensor 15 may perform a detection of the open state and the closed state of the window of the vehicle 1. The processor 20 may perform the process of permitting or forbidding the driver to drive the vehicle 1, based on the amount of the alcohol component included in the breath of the driver.

FIG. 3 illustrates an operation example of the alcohol detection apparatus 10.

First, the alcohol detection apparatus 10 may confirm whether the door and the window are closed in a state where the driver is present in the driver's seat (step S101). For example, the image recognition processing unit 21 may detect whether the driver is present in the driver's seat by performing the image recognition process based on the captured image supplied from the image sensor 11. Further, the processor 20 may confirm whether all the doors of the vehicle 1 and all the windows of the vehicle 1 are closed, based on the respective results of the detections performed by the door sensor 14 and the window sensor 15. Note that this is non-limiting, and in one example, the processor 20 may detect whether a door near the driver's seat and a window near the driver's seat of the vehicle 1 are closed based on the respective results of the detections performed by the door sensor 14 and the window sensor 15. If any of the door and the window is not closed (step S102: N), the process may proceed to step S115.

If the door and the window are closed in step S102 (step S102: Y), the alcohol detection apparatus 10 may confirm whether an occupant other than the driver is absent around the driver's seat (step S103). For example, the image recognition processing unit 21 may confirm whether an occupant other than the driver is not leaning over the driver's seat from a seat other than the driver's seat by performing the image recognition process based on the captured image supplied from the image sensor 11 If the door and the window are closed and an occupant other than the driver is absent around the driver's seat, a possibility may be low that a detection of alcohol is performed based on breath of a person other than the driver. Therefore, it may be highly possible that the result of the detection obtainable by the alcohol sensor 13 is effective. If an occupant other than the driver is present around the driver's seat (step S104: N), the process may proceed to step S115.

If an occupant other than the driver is absent around the driver's seat in step S104 (step S104: Y), the processor 20 of the alcohol detection apparatus 10 may confirm whether the touch sensor 12 provided at the steering wheel is detecting a touch (step S105). If the touch sensor 12 is not detecting any touch (step S106: N), the process may proceed to step S115.

If the touch sensor 12 detects a touch in step S106 (step S106: Y), the alcohol detection apparatus 10 may confirm whether the driver's hand is holding the steering wheel (step S107). For example, the skeleton determination processing unit 22 may detect whether the driver's hand is holding the steering wheel by performing the skeleton determination process based on the captured image supplied from the image sensor 11. If the driver's hand is not holding the steering wheel (step S108: N), the process may proceed to step S115. If the driver's hand is holding the steering wheel in step S108 (step S108: Y), the alcohol detection apparatus 10 may confirm whether the alcohol sensor 13 is detected (step S109). For example, the image recognition processing unit 21 may detect the marker of the alcohol sensor 13 by performing the image recognition process based on the captured image supplied from the image sensor 11. If the marker of the alcohol sensor 13 is detected, the image recognition processing unit 21 may determine that the alcohol sensor 13 is detected. If the alcohol sensor 13 is not detected by the image recognition processing unit 21 (step S109: N), the process in step S109 may be repeated until the image recognition processing unit 21 detects the alcohol sensor 13.

If the image recognition processing unit 21 detects the alcohol sensor 13 in step S109 (step S109: Y), the alcohol detection apparatus 10 may confirm whether the driver's hand is holding the alcohol sensor 13 (step S110). For example, the skeleton determination processing unit 22 may determine whether the driver is holding the alcohol sensor 13 by his or her hand other than the hand holding the steering wheel, by performing the skeleton determination process based on the captured image supplied from the image sensor 11. If the driver is holding the steering wheel by one hand and is holding the alcohol sensor 13 by another hand, for example, a possibility may be low that a wrong act such as using breath of another person stored in a balloon for the detection of alcohol is performed. Therefore, it may be highly possible that the result of the detection obtainable by the alcohol sensor 13 is effective. If the driver's hand is not holding the alcohol sensor 13 (step S111: N), the process may proceed to step S115.

If the driver's hand is holding the alcohol sensor 13 in step S111 (step S111: Y), the alcohol detection apparatus 10 may confirm whether the driver is breathing into the alcohol sensor 13, based on the distance from the driver's face to the alcohol sensor 13 (step S112). For example, the distance calculation processing unit 23 may calculate the distance from the driver's face to the blowing port of the alcohol sensor 13 by performing the distance calculation process based on the captured image supplied from the image sensor 11. Further, the distance calculation processing unit 23 may confirm whether the driver is breathing into the blowing port of the alcohol sensor 13 by confirming whether the calculated distance is less than or equal to a predetermined distance. The predetermined distance may be about 10 cm, for example. If the driver is breathing into the alcohol sensor 13, it may be highly possible that the detection of alcohol is performed based on the breath of the driver. Accordingly, it may be highly possible that the result of the detection obtainable by the alcohol sensor 13 is effective. If the driver is not breathing into the alcohol sensor 13 (step S113: N), the process may proceed to step S115.

If the driver is breathing into the alcohol sensor 13 in step S113 (step S113: Y), the determination processing unit 24 may determine that the result of the detection obtainable by the alcohol sensor 13 is effective (step S114). That is, the alcohol detection apparatus 10 may determine that it is highly possible that the detection of alcohol is performed based on the breath of the driver based on the processes in steps S101 to S113, and may determine that the result of the determination obtainable by the alcohol sensor 13 is effective. Thereafter, the process may proceed to step S116.

In contrast, if any of the door and the window is not closed in step S102 (step S102: N), if an occupant other than the driver is present around the driver's seat in step S104 (step S104: N), if the touch sensor 12 does not detect any touch in step S106 (step S106: N), if the driver's hand is not holding the steering wheel in step S108 (step S108: N), if the driver's hand is not holding the alcohol sensor 13 in step S111 (step S111: N), or if the driver is not breathing into the blowing port of the alcohol sensor 13 in step S113 (step S113: N), the determination processing unit 24 may determine that the result of the detection obtainable by the alcohol sensor 13 is not effective (step S115). That is, the alcohol detection apparatus 10 may determine that there is a possibility that the detection of alcohol is not performed based on the breath of the driver based on the processes in steps S101 to S113, and may determine that the result of the detection obtainable by the alcohol sensor 13 is not effective. Thereafter, the process may proceed to step S119.

If it is determined that the result of the detection obtainable by the alcohol sensor 13 is effective, the processor 20 of the alcohol detection apparatus 10 may thereafter confirm the amount of the alcohol component included in the breath of the driver based on the result of the detection obtained by the alcohol sensor 13 (step S116).

If the amount of the alcohol component included in the breath of the driver is less than or equal to the predetermined amount (step S117: Y), the determination processing unit 24 may permit the driver to drive the vehicle 1 (step S118). Further, the determination processing unit 24 may allow the engine of the vehicle 1 to be started, for example. This may be the end of this flow.

If the determination processing unit 24 determines that the result of the determination obtainable by the alcohol sensor 13 is not effective in step S115, or if the amount of the alcohol component included in the breath of the driver is not less than or equal to the predetermined amount (step S117: N), the determination processing unit 24 may forbid the driver to drive the vehicle 1 (step S119). Further, the determination processing unit 24 may inhibit the engine of the vehicle 1 from being started, for example. This may be the end of this flow.

As described above, the alcohol detection apparatus 10 incudes the image sensor 11, the touch sensor 12, the alcohol sensor 13, and the processor 20. The image sensor 11 is configured to generate the captured image by performing imaging of the occupant in the driver's seat of the vehicle 1. The touch sensor 12 is provided at the driver's seat and is configured to perform a detection of a touch. The alcohol sensor 13 is configured to perform a detection of the alcohol component included in the breath of the occupant. The processor 20 is configured to perform processes based on the captured image generated by the image sensor 11, the result of the detection performed by the touch sensor 12, and the result of the detection performed by the alcohol sensor 13. The processor 20 is configured to perform a first process of confirming, based on the captured image, whether the occupant in the driver's seat is touching the touch sensor 12. The processor 20 is configured to perform a second process of confirming, based on the captured image, whether the occupant in the driver's seat is holding the alcohol sensor 13. The processor 20 is configured to perform a determination process of determining that the result of the detection obtainable by the alcohol sensor 13 is effective when a plurality of conditions is satisfied. The plurality of conditions include that the occupant is touching the touch sensor 12 in the first process and that the occupant is holding the alcohol sensor 13 in the second process. When the occupant in the driver's seat is touching the touch sensor 12 by holding the steering wheel and is holding the alcohol sensor 13, both hands of the occupant may be prevented from being free. In this case, for example, a possibility may be low that the occupant performs a wrong act such as using breath of another person stored in a balloon for the detection of alcohol. Therefore, a reliability of the result of the detection obtainable by the alcohol sensor 13 may increase. Accordingly, the processor 20 may determine that the result of the detection obtainable by the alcohol sensor 13 is effective. For example, when it is determined that the result of the detection obtainable by the alcohol sensor 13 is effective, the alcohol detection apparatus 10 may permit or forbid the occupant to drive the vehicle 1 based on the result of the detection obtained by the alcohol sensor 13. When it is determined that the result of the detection obtainable by the alcohol sensor 13 is not effective, the alcohol detection apparatus 10 may forbid the occupant to drive the vehicle 1. Accordingly, the alcohol detection apparatus 10 makes it possible to more effectively detect whether the occupant has drunk alcohol.

In the alcohol detection apparatus 10, the processor 20 may be configured to further perform a third process of calculating the distance from the face of the occupant in the driver's seat to the alcohol sensor 13 based on the captured image. The plurality of conditions may further include that the distance is less than or equal to the predetermined distance in the third process. When the distance from the face of the occupant to the alcohol sensor 13 is less than or equal to the predetermined distance, it may be highly possible that the detection of alcohol is performed based on the breath of the occupant. Therefore, the reliability of the result of the detection obtainable by the alcohol sensor 13 may increase. Accordingly, the processor 20 may determine that the result of the detection obtainable by the alcohol sensor 13 is effective. As a result, the alcohol detection apparatus 10 makes it possible to more effectively detect whether the occupant has drunk alcohol.

In the alcohol detection apparatus 10, the processor 20 may be configured to further perform a fourth process of confirming, based on the captured image, whether another occupant other than the occupant is present around the driver's seat. The plurality of conditions may further include that the other occupant other than the occupant is not present around the driver's seat in the fourth process. When the other occupant other than the occupant is not present around the driver's seat, it may be highly possible that the detection of alcohol is performed based on the breath of the occupant. Therefore, the reliability of the result of the detection obtainable by the alcohol sensor 13 may increase. Accordingly, the processor 20 may determine that the result of the detection obtainable by the alcohol sensor 13 is effective. As a result, the alcohol detection apparatus 10 makes it possible to more effectively detect whether the occupant has drunk alcohol.

In the alcohol detection apparatus 10, the processor 20 may be configured to further perform a fifth process of confirming, based on the captured image, whether the door and the window of the vehicle 1 are closed. The plurality of conditions may further include that the door and the window of the vehicle 1 are closed in the fifth process. When the door and the window of the vehicle 1 are closed, it may be highly possible that the detection of alcohol is performed based on the breath of the occupant. Therefore, the reliability of the result of the detection obtainable by the alcohol sensor 13 may increase. Accordingly, the processor 20 may determine that the result of the detection obtainable by the alcohol sensor 13 is effective. As a result, the alcohol detection apparatus 10 makes it possible to more effectively detect whether the occupant has drunk alcohol.

In the alcohol detection apparatus 10, the first process may include confirming whether a first hand of the occupant in the driver's seat is touching the touch sensor 12. The second process may include confirming whether a second hand of the occupant in the driver's seat is holding the alcohol sensor 13. When the occupant in the driver's seat is touching the touch sensor 12 by the first hand and is holding the alcohol sensor 13 by the second hand, both hands of the occupant may be prevented from being free. In this case, for example, the possibility may be low that the occupant performs a wrong act such as using breath of another person stored in a balloon for the detection of alcohol. Therefore, the reliability of the result of the detection obtainable by the alcohol sensor 13 may increase. Accordingly, the processor 20 may determine that the result of the detection obtainable by the alcohol sensor 13 is effective. As a result, the alcohol detection apparatus 10 makes it possible to more effectively detect whether the occupant has drunk alcohol.

As described above, according to the example embodiment of the disclosure, an image sensor, a touch sensor, an alcohol sensor, and a processor are provided. The image sensor is configured to generate a captured image by performing imaging of a first occupant in a driver's seat of a vehicle. The touch sensor is provided at the driver's seat and is configured to perform a detection of a touch. The alcohol sensor is configured to perform a detection of an alcohol component included in breath of the first occupant. The processor is configured to perform processes based on the captured image generated by the image sensor, a result of the detection performed by the touch sensor, and a result of the detection performed by the alcohol sensor. The processor is configured to perform a first process of confirming, based on the captured image, whether the first occupant in the driver's seat is touching the touch sensor. The processor is configured to perform a second process of confirming, based on the captured image, whether the first occupant in the driver's seat is holding the alcohol sensor. The processor is configured to perform a determination process of determining that the result of the detection obtainable by the alcohol sensor is effective when a plurality of conditions is satisfied. The plurality of conditions includes that the first occupant is touching the touch sensor in the first process and that the first occupant is holding the alcohol sensor in the second process. It is therefore possible to more effectively detect whether an occupant has drunk alcohol.

According to the example embodiment of the disclosure, the processor may be configured to further perform a third process of calculating a distance from a face of the first occupant in the driver's seat to the alcohol sensor based on the captured image. The plurality of conditions may further include that the distance is less than or equal to a predetermined distance in the third process. It is therefore possible to more effectively detect whether an occupant has drunk alcohol.

According to the example embodiment of the disclosure, the processor may be configured to further perform a fourth process of confirming, based on the captured image, whether a second occupant other than the first occupant is present around the driver's seat. The plurality of conditions may further include that the second occupant other than the first occupant is not present around the driver's seat in the fourth process. It is therefore possible to more effectively detect whether an occupant has drunk alcohol.

According to the example embodiment of the disclosure, the processor may be configured to further perform a fifth process of confirming, based on the captured image, whether a door and a window of the vehicle are closed. The plurality of conditions may further include that the door and the window of the vehicle are closed in the fifth process. It is therefore possible to more effectively detect whether an occupant has drunk alcohol.

According to the example embodiment of the disclosure, the first process may include confirming whether a first hand of the first occupant in the driver's seat is touching the touch sensor. The second process may include confirming whether a second hand of the first occupant in the driver's seat is holding the alcohol sensor. It is therefore possible to more effectively detect whether an occupant has drunk alcohol.

Figure 3A:
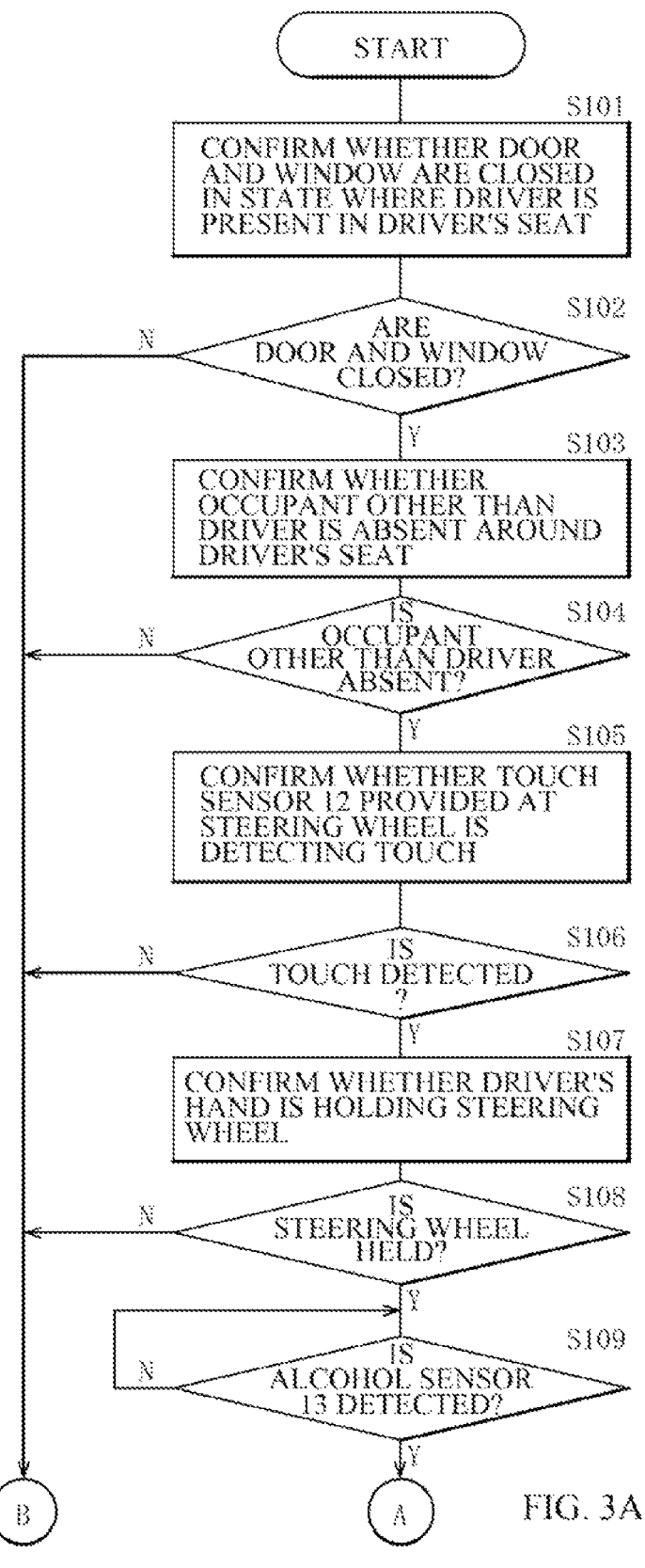
FIG. 3A is a flowchart illustrating an operation example of the alcohol detection apparatus illustrated in FIG. 2.
Figure 3B:
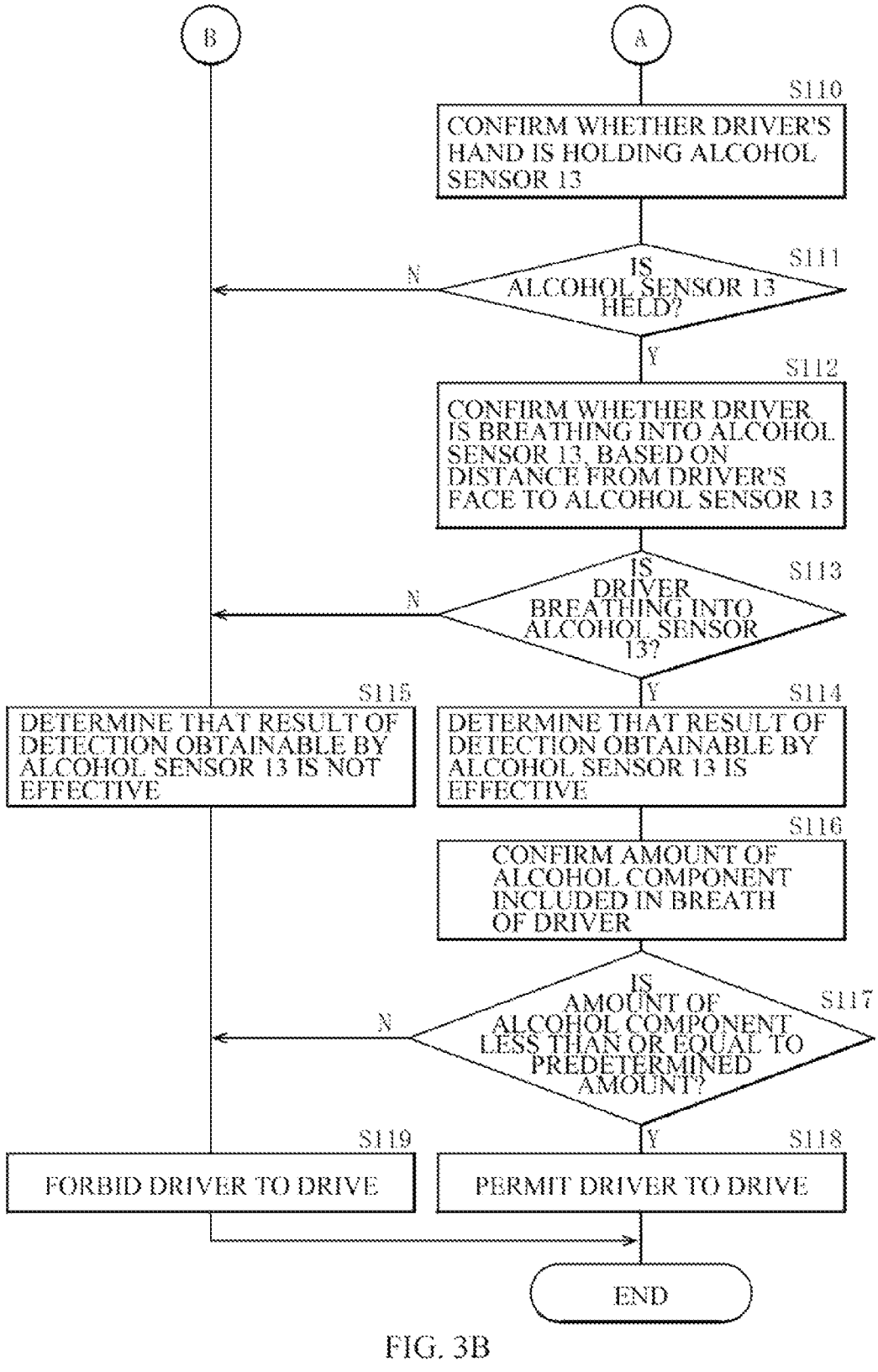
FIG. 3B is another flowchart illustrating the operation example of the alcohol detection apparatus illustrated in FIG. 2.

In the example embodiment described above, the processes may be performed in the order illustrated in FIGS. 3A and 3B; however, the order of the processes is not limited thereto, and may be changed appropriately, for example.

In the example embodiment described above, as illustrated in FIGS. 3A and 3B, it may be determined whether the result of the detection obtainable by the alcohol sensor 13 is effective, and the alcohol sensor 13 may detect the alcohol component if it is determined that the result of the detection obtainable by the alcohol sensor 13 is effective; however, this is non-limiting. Alternatively, the alcohol sensor 13 may detect the alcohol component, and it may be thereafter determined whether the result of the detection obtained by the alcohol sensor 13 is effective.

In the example embodiment described above, the touch sensor 12 may be provided at the steering wheel; however, a position to provide the touch sensor 12 is not limited thereto, and the touch sensor 12 may be provided at various positions where the driver is able to touch. For example, the touch sensor 12 may be provided at a gear shift lever that allows for an operation of a transmission. For example, the touch sensor 12 may be provided at a device which the driver is able to hold firmly. In this case, the driver's hand firmly holding the device may prevent the driver's hand from being free. This may decrease a possibility that the driver performs a wrong act. As a result, it is possible to more effectively detect whether an occupant has drunk alcohol.

Further, two or more of the foregoing modifications may be combined with each other.

Although some example embodiments of the disclosure have been described in the foregoing by way of example with reference to the accompanying drawings, the disclosure is by no means limited to the embodiments described above. It should be appreciated that modifications and alterations may be made by persons skilled in the art without departing from the scope as defined by the appended claims. The disclosure is intended to include such modifications and alterations in so far as they fall within the scope of the appended claims or the equivalents thereof.

For example, the processes illustrated in FIGS. 3A and 3B are mere examples, and some of the processes may be omitted or any other process may be additionally provided.

The effects described herein are mere examples, and effects of an embodiment of the disclosure are not limited thereto. Accordingly, any other effect may be obtained in relation to the embodiment of the disclosure.

An embodiment of the disclosure may have any of the following configurations.

(1)
An alcohol detection apparatus including:
an image sensor configured to generate a captured image by performing imaging of a first occupant in a driver's seat of a vehicle;
a touch sensor provided at the driver's seat and configured to perform a detection of a touch;
an alcohol sensor configured to perform a detection of an alcohol component included in breath of the first occupant; and
a processor configured to perform processes based on the captured image generated by the image sensor, a result of the detection performed by the touch sensor, and a result of the detection performed by the alcohol sensor, in which
the processor is configured to
   perform a first process of confirming, based on the captured image, whether the first occupant in the driver's seat is touching the touch sensor,
   perform a second process of confirming, based on the captured image, whether the first occupant in the driver's seat is holding the alcohol sensor, and
   perform a determination process of determining that the result of the detection obtainable by the alcohol sensor is effective when a plurality of conditions is satisfied, the plurality of conditions including that the first occupant is touching the touch sensor in the first process and that the first occupant is holding the alcohol sensor in the second process.

(2)
The alcohol detection apparatus according to (1) described above, in which
the processor is configured to further perform a third process of calculating a distance from a face of the first occupant in the driver's seat to the alcohol sensor based on the captured image, and
the plurality of conditions further includes that the distance is less than or equal to a predetermined distance in the third process.

(3)
The alcohol detection apparatus according to (1) or (2) described above, in which
the processor is configured to further perform a fourth process of confirming, based on the captured image, whether a second occupant other than the first occupant is present around the driver's seat, and
the plurality of conditions further includes that the second occupant other than the first occupant is not present around the driver's seat in the fourth process.

(4)
The alcohol detection apparatus according to any one of (1) to (3) described above, in which
the processor is configured to further perform a fifth process of confirming, based on the captured image, whether a door and a window of the vehicle are closed, and
the plurality of conditions further includes that the door and the window of the vehicle are closed in the fifth process.

(5)
The alcohol detection apparatus according to any one of (1) to (4) described above, in which
the first process includes confirming whether a first hand of the first occupant in the driver's seat is touching the touch sensor, and
the second process includes confirming whether a second hand of the first occupant in the driver's seat is holding the alcohol sensor.

The processor 20 illustrated in FIG. 2 is implementable by circuitry including at least one semiconductor integrated circuit such as at least one processor (e.g., a central processing unit (CPU)), at least one application specific integrated circuit (ASIC), and/or at least one field programmable gate array (FPGA). At least one processor is configurable, by reading instructions from at least one machine readable non-transitory tangible medium, to perform all or a part of functions of the processor 20 illustrated in FIG. 2. Such a medium may take many forms, including, but not limited to, any type of magnetic medium such as a hard disk, any type of optical medium such as a CD and a DVD, any type of semiconductor memory (i.e., semiconductor circuit) such as a volatile memory and a non-volatile memory. The volatile memory may include a DRAM and a SRAM, and the nonvolatile memory may include a ROM and a NVRAM. The ASIC is an integrated circuit (IC) customized to perform, and the FPGA is an integrated circuit designed to be configured after manufacturing in order to perform, all or a part of the functions of the processor 20 illustrated in FIG. 2.

The invention claimed is:

1. An alcohol detection apparatus comprising:
an image sensor configured to generate a captured image by performing imaging of a first occupant in a driver's seat of a vehicle;
a touch sensor provided at a position where the first occupant is able to touch the touch sensor with a first hand of the first occupant and configured to perform a detection of a touch;
an alcohol sensor configured to be held by a second hand of the first occupant and to perform a detection of an alcohol component included in breath exhaled from a mouth or nose of the first occupant, the second hand being different from the first hand; and
a processor configured to perform processes based on the captured image generated by the image sensor, a result of the detection performed by the touch sensor, and a result of the detection performed by the alcohol sensor, wherein,
the processor is configured to:
perform a first process of confirming, based on the captured image, whether the first hand of the first occupant is touching the touch sensor,
perform a second process of confirming, based on the captured image, whether the second hand of the first occupant is holding the alcohol sensor, and perform a determination process of determining that the result of the detection obtainable by the alcohol sensor is effective when a plurality of conditions is satisfied, the plurality of conditions comprising (i) that the touch sensor detects the touch, (ii) that the first hand of the first occupant is touching the touch sensor in the first process and (iii) that the second hand of the first occupant is holding the alcohol sensor in the second process.

2. The alcohol detection apparatus according to claim 1, wherein
the processor is configured to further perform a third process of calculating a distance from a face of the first occupant in the driver's seat to the alcohol sensor based on the captured image, and
the plurality of conditions further comprises that the distance is less than or equal to a predetermined distance in the third process.

3. The alcohol detection apparatus according to claim 1, wherein
the processor is configured to further perform a fourth process of confirming, based on the captured image, whether a second occupant other than the first occupant is present around the driver's seat, and
the plurality of conditions further comprises that the second occupant other than the first occupant is not present around the driver's seat in the fourth process.

4. The alcohol detection apparatus according to claim 1, wherein
the processor is configured to further perform a fifth process of confirming, based on the captured image, whether a door and a window of the vehicle are closed, and
the plurality of conditions further comprises that the door and the window of the vehicle are closed in the fifth process.

5. The alcohol detection apparatus according to claim 1, wherein confirming whether the first hand is touching the touch sensor and confirming whether the second hand is holding the alcohol sensor are performed by a skeleton determination process based on the captured image.

6. The alcohol detection apparatus according to claim 1, wherein the touch sensor is provided at a steering wheel of the vehicle.

7. The alcohol detection apparatus according to claim 5, wherein the touch sensor is provided at a steering wheel of the vehicle.

* * * * *